(12) United States Patent
Blood et al.

(10) Patent No.: US 10,835,151 B2
(45) Date of Patent: Nov. 17, 2020

(54) SENSOR ASSEMBLIES FOR ELECTROMAGNETIC NAVIGATION SYSTEMS

(71) Applicant: Boston Scientific Scimed Inc., Maple Grove, MN (US)

(72) Inventors: James E. Blood, Shoreview, MN (US); Daniel J. Foster, Lino Lakes, MN (US); Steven J. Meyer, Lake Elmo, MN (US); David A. Chizek, Brooklyn Park, MN (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 403 days.

(21) Appl. No.: 15/888,834

(22) Filed: Feb. 5, 2018

(65) Prior Publication Data

US 2018/0220929 A1    Aug. 9, 2018

Related U.S. Application Data

(60) Provisional application No. 62/455,329, filed on Feb. 6, 2017.

(51) Int. Cl.
*A61B 5/06* (2006.01)
*G01D 5/20* (2006.01)
(Continued)

(52) U.S. Cl.
CPC .............. *A61B 5/062* (2013.01); *G01D 5/16* (2013.01); *G01D 5/20* (2013.01); *G01R 33/0206* (2013.01);
(Continued)

(58) Field of Classification Search
None
See application file for complete search history.

(56) References Cited

U.S. PATENT DOCUMENTS 5,644,230 A    7/1997 Pant et al.
5,994,989 A    11/1999 Rowe et al.
(Continued)

FOREIGN PATENT DOCUMENTS

EP    0696357 B1    2/1996
JP    2003-502876 A    1/2003
(Continued)

OTHER PUBLICATIONS

Mönch et al., "Rolled-up magnetic sensor: nanomembrane architecture for in-flow detection of magnetic objects". ACS Nano, vol. 5, No. 9, pp. 7436-7442. 2011. (Year: 2011).*
(Continued)

*Primary Examiner* — Katherine L Fernandez
*Assistant Examiner* — Yi-Shan Yang
(74) *Attorney, Agent, or Firm* — Faegre Drinker Biddle & Reath LLP (57) ABSTRACT

A sensor assembly includes a substrate including a first portion, a second portion, and a rolled section positioned between the first portion and the second portion. The sensor assembly further includes a first magnetic field sensor coupled to the first portion. The first magnetic field sensor has a primary sensing direction aligned with a longitudinal axis of the sensor assembly. The sensor assembly further includes a second magnetic field sensor coupled to the second portion. The rolled section is shaped such that the second magnetic field sensor is oriented with respect to the first magnetic field sensor so that the second magnetic field sensor has a primary sensing direction aligned with an axis orthogonal to the longitudinal axis.

20 Claims, 8 Drawing Sheets

(51) Int. Cl.
  *G01D 5/16*   (2006.01)
  *G01R 33/02*  (2006.01)
  *G01R 33/09*  (2006.01)

(52) U.S. Cl.
  CPC .... *G01R 33/098* (2013.01); *A61B 2562/0223* (2013.01)

(56) References Cited

U.S. PATENT DOCUMENTS

| | | |
|---|---|---|
| 6,169,254 B1 | 1/2001 | Pant et al. |
| 6,183,889 B1 | 2/2001 | Koshiba et al. |
| 6,184,680 B1 | 2/2001 | Shinoura et al. |
| 6,273,322 B1 | 8/2001 | Yamamoto et al. |
| 6,484,118 B1 | 11/2002 | Govari |
| 6,501,678 B1 | 12/2002 | Lenssen et al. |
| 6,536,123 B2 | 3/2003 | Tamura |
| 6,593,884 B1 | 7/2003 | Gilboa et al. |
| 6,690,963 B2 | 2/2004 | Ben-Haim et al. |
| 6,836,971 B1 | 1/2005 | Wan |
| 7,301,332 B2 | 11/2007 | Govari et al. |
| 7,870,678 B2 | 1/2011 | Kwon et al. |
| 8,390,279 B2 | 3/2013 | Klocke et al. |
| 8,391,952 B2 | 3/2013 | Anderson |
| 8,750,961 B1 | 6/2014 | Ries et al. |
| 9,002,675 B2 | 4/2015 | McIntyre et al. |
| 9,801,563 B2 * | 10/2017 | Bernstein ............ A61B 5/6868 |
| 2002/0026197 A1 | 2/2002 | Foley et al. |
| 2003/0123198 A1 | 7/2003 | Sugawara et al. |
| 2003/0231098 A1 | 12/2003 | Wan |
| 2004/0124835 A1 | 7/2004 | Kimura |
| 2007/0080682 A1 * | 4/2007 | Govari ............... G01R 33/0206 324/247 |
| 2007/0200564 A1 | 8/2007 | Motz et al. |
| 2007/0260139 A1 | 11/2007 | Minai et al. |
| 2008/0052931 A1 | 3/2008 | Kwon et al. |
| 2008/0052932 A1 | 3/2008 | Xue et al. |
| 2010/0171492 A1 | 7/2010 | Klocke et al. |
| 2011/0234218 A1 | 9/2011 | Lagouge |
| 2011/0248706 A1 | 10/2011 | Davis et al. |
| 2012/0038357 A1 | 2/2012 | Brandon et al. |
| 2012/0081111 A1 | 4/2012 | Kim et al. |
| 2012/0153942 A1 | 6/2012 | Van et al. |
| 2012/0299587 A1 | 11/2012 | Rieger et al. |
| 2013/0127454 A1 | 5/2013 | Ungaretti et al. |
| 2013/0169272 A1 | 7/2013 | Eichler et al. |
| 2014/0276004 A1 * | 9/2014 | Strupeck ............. A61B 5/061 600/424 |
| 2014/0327437 A1 | 11/2014 | Han et al. |
| 2015/0087921 A1 | 3/2015 | Felix et al. |
| 2016/0135668 A1 * | 5/2016 | Gat ...................... A61B 5/062 600/118 |
| 2016/0245877 A1 | 8/2016 | Deak |
| 2017/0021172 A1 | 1/2017 | Perez et al. |
| 2017/0059361 A1 | 3/2017 | Nagarkar et al. |
| 2017/0325715 A1 | 11/2017 | Mehendale et al. |
| 2018/0042518 A1 | 2/2018 | Fruci et al. |
| 2018/0132360 A1 * | 5/2018 | Wang .................... B23K 20/24 |
| 2018/0153436 A1 | 6/2018 | Olson |
| 2018/0168482 A1 | 6/2018 | Hein |
| 2018/0172420 A1 | 6/2018 | Hein et al. |
| 2018/0172865 A1 | 6/2018 | Hein et al. |
| 2018/0220928 A1 | 8/2018 | Blood et al. |

FOREIGN PATENT DOCUMENTS

| | | |
|---|---|---|
| JP | 2007-147593 A | 6/2007 |
| JP | 2012-523566 A | 10/2012 |
| WO | 1995009562 A1 | 4/1995 |
| WO | 2014207738 A1 | 12/2014 |
| WO | 2016087970 A1 | 6/2016 |
| WO | 2016196985 A1 | 12/2016 |

OTHER PUBLICATIONS

International Search Report and Written Opinion issued in PCT/US2017/067111, dated May 8, 2018, 19 pages.
International Search Report and Written Opinion issued in PCT/US2018/016895, dated Apr. 13, 2018, 11 pages.
International Search Report and Written Opinion issued in PCT/US2018016876, dated Apr. 11, 2018, 10 pages.
PCT Invitation to Pay Additional Fees issued in PCT/US2017067111, dated Mar. 15, 2018, 16 pages.

* cited by examiner

SENSOR ASSEMBLIES FOR ELECTROMAGNETIC NAVIGATION SYSTEMS

CROSS-REFERENCE TO RELATED APPLICATION

This application claims priority to Provisional Application No. 62/455,329, filed Feb. 6, 2017, which is herein incorporated by reference in its entirety.

TECHNICAL FIELD

The present disclosure relates to systems, methods, and devices for tracking items. More specifically, the disclosure relates to systems, methods, and devices for electro-magnetically tracking medical devices used in medical procedures.

BACKGROUND

A variety of systems, methods, and devices can be used to track medical devices. Tracking systems can use externally generated magnetic fields that are sensed by at least one tracking sensor in the tracked medical device. The externally generated magnetic fields provide a fixed frame of reference, and the tracking sensor senses the magnetic fields to determine the location and orientation of the sensor in relation to the fixed frame of reference.

SUMMARY

In Example 1, a sensor assembly includes a substrate including a first portion, a second portion, and a rolled section positioned between the first portion and the second portion. The sensor assembly further includes a first magnetic field sensor coupled to the first portion. The first magnetic field sensor has a primary sensing direction aligned with a longitudinal axis of the sensor assembly. The sensor assembly further includes a second magnetic field sensor coupled to the second portion. The rolled section is shaped such that the second magnetic field sensor is oriented with respect to the first magnetic field sensor so that the second magnetic field sensor has a primary sensing direction aligned with an axis orthogonal to the longitudinal axis.

In Example 2, the sensor assembly of Example 1, further comprising a third magnetic field sensor coupled to the first portion and oriented with respect to the first magnetic field sensor such that the third magnetic field sensor has a primary sensing direction aligned with an axis orthogonal to the longitudinal axis.

In Example 3, the sensor assembly of any of Examples 1-2, wherein the sensor assembly extends along a longitudinal axis, and wherein the rolled section is rolled around the longitudinal axis.

In Example 4, the sensor assembly of Example 3, wherein the rolled section is rolled around the longitudinal axis by at least 180 degrees.

In Example 5, the sensor assembly of any of Examples 3-4, wherein the rolled section is rolled around the longitudinal axis by at least 360 degrees.

In Example 6, the sensor assembly of Example 3, wherein the rolled section is rolled around the longitudinal axis between 90 and 180 degrees.

In Example 7, the sensor assembly of Example 3, wherein the rolled section is rolled around the longitudinal axis between 180 and 360 degrees.

In Example 8, the sensor assembly of any of Examples 1-7, wherein the first, second, and third magnetic field sensors include one of inductive sensing coils, magneto-resistive sensing elements, giant magneto-impedance sensing elements, and flux-gate sensing elements.

In Example 9, the sensor assembly of Example 8, wherein the magneto-resistive sensing elements include one of anisotropic magneto-resistive sensing elements, giant magneto-resistive sensing elements, tunneling magneto-resistive sensing elements, Hall effect sensing elements, colossal magneto-resistive sensing elements, extraordinary magneto-resistive sensing elements, and spin Hall sensing elements.

In Example 10, the sensor assembly of any of Examples 1-9, wherein the substrate forms part of a flex circuit.

In Example 11, the sensor assembly of any of Examples 1-10, wherein the magnetic field sensors are electrically coupled to conductors.

In Example 12, the sensor assembly of any of Examples 1-11, wherein the magnetic field sensors are wire bonded to conductors.

In Example 13, the sensor assembly of any of Examples 1-12, wherein the magnetic field sensors are coupled to conductors via a flip-chip approach.

In Example 14, the sensor assembly of any of Examples 1-13, wherein the sensing assembly forms a cylinder shape.

In Example 15, the sensor assembly of any of Examples 1-14, wherein the rolled section forms a cylinder shape.

In Example 16, the sensor assembly of any of Examples 1-15, wherein the first portion and the second portion are substantially flat.

In Example 17, the sensor assembly of any of Examples 1-16, wherein the rolled section has a length along the longitudinal axis that is substantially equal to an overall length of the sensor assembly.

In Example 18, the sensor assembly of any of Examples 1-16, wherein the rolled section includes a first arm and a second arm.

In Example 19, a method for making the sensor assembly of any of Examples 1-18, the method including bending the rolled section such that the primary sensing directions of the first and second magnetic field sensors are oriented orthogonal to each other.

In Example 20, a medical probe including a distal portion having a sensor assembly, wherein the sensor assembly comprises the sensor assembly of any of Examples 1-18.

In Example 21, a medical system includes the medical probe according to Example 20, a magnetic field generator configured to generate a multi-dimensional magnetic field in a volume including the medical probe and a patient, and a processor operable to receive outputs from the sensor assembly to determine a position of the sensor assembly within the volume.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the disclosure is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the invention as defined by the appended claims.

DETAILED DESCRIPTION

During medical procedures, medical devices such as probes (e.g., diagnostic and therapeutic catheters, introducers, guidewires, endoscopic probes and cannulae, and the like) are inserted into a patient through the patient's vascular system and/or a catheter lumen. To track the location and orientation of a probe within the patient, probes can be provisioned with magnetic field sensors.

Figure 1:
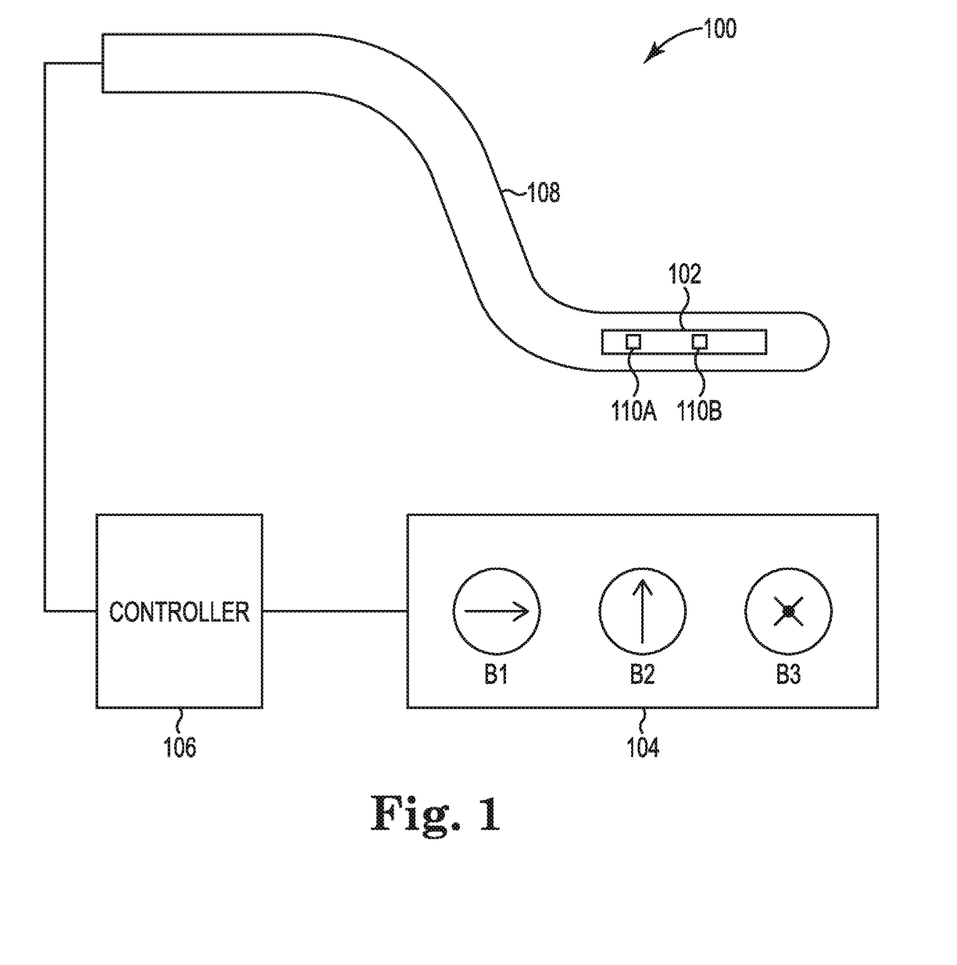
FIG. 1 shows a schematic of a tracking system, in accordance with certain embodiments of the present disclosure.

FIG. 1 is a diagram illustrating a tracking system 100 including a sensor assembly 102, magnetic field generator 104, a controller 106, and a probe 108 (e.g., catheter, imaging probe, diagnostic probe). The sensor assembly 102 can be positioned within the probe 108, for example, at a distal end of the probe 108. The tracking system 100 is configured to determine the location and orientation of the sensor assembly 102 and, therefore, the probe 108. Magnetic fields generated by the magnetic field generator 104 provide a frame of reference for the tracking system 100 such that the location and orientation of the sensor assembly 102 is determined relative to the generated magnetic fields. The tracking system 100 can be used in a medical procedure, where the probe 108 is inserted into a patient and the sensor assembly 102 is used to assist with tracking the location of the probe 108 in the patient.

The sensor assembly 102 is communicatively coupled to the controller 106 by a wired or wireless communications path such that the controller 106 sends and receives various signals to and from the sensor assembly 102. The magnetic field generator 104 is configured to generate one or more magnetic fields. For example, the magnetic field generator 104 is configured to generate at least three magnetic fields B1, B2, and B3. Each of the magnetic fields B1, B2, and B3 is directed in a different direction, as indicated by arrows in FIG. 1. Magnetic field B1 is a magnetic field in the horizontal direction, magnetic field B2 is a magnetic field in the vertical direction, and magnetic field B3 is a magnetic field into the page of FIG. 1. The controller 106 is configured to control the magnetic field generator 104 via a wired or wireless communications path to generate one or more of the magnetic fields B1, B2, and B3 to assist with tracking the sensor assembly 102 (and therefore probe 108).

The sensor assembly 102 is configured to sense the generated magnetic fields and provide tracking signals indicating the location and orientation of the sensor assembly 102 in up to six degrees of freedom (i.e., x, y, and z measurements, and pitch, yaw, and roll angles). Generally, the number of degrees of freedom that a tracking system is able to track depends on the number of magnetic field sensors and magnetic field generators. For example, a tracking system with a single magnetic field sensor may not be capable of tracking roll angles and thus are limited to tracking in only five degrees of freedom (i.e., x, y, and z coordinates, and pitch and yaw angles). This is because a magnetic field sensed by a single magnetic field sensor does not change as the single magnetic field sensor is "rolled." As such, the sensor assembly 102 includes at least two magnetic field sensors, 110A and 110B. The magnetic field sensors can include sensors such as inductive sensing coils and/or various sensing elements such as magneto-resistive (MR) sensing elements (e.g., anisotropic magneto-resistive (AMR) sensing elements, giant magneto-resistive (GMR) sensing elements, tunneling magneto-resistive (TMR) sensing elements, Hall effect sensing elements, colossal magneto-resistive (CMR) sensing elements, extraordinary magneto-resistive (EMR) sensing elements, spin Hall sensing elements, and the like), giant magneto-impedance (GMI) sensing elements, and/or flux-gate sensing elements. In addition, the sensor assembly 102 and/or the probe 108 can feature other types of sensors, such as temperature sensors, ultrasound sensors, etc.

The sensor assembly 102 is configured to sense each of the magnetic fields B1, B2, and B3 and provide signals to the controller 106 that correspond to each of the sensed magnetic fields B1, B2, and B3. The controller 106 receives the signals from the sensor assembly 102 via the communications path and determines the position and location of the sensor assembly 102 and probe 108 in relation to the generated magnetic fields B1, B2, and B3.

The magnetic field sensors, 110A and 110B, can be powered by voltages or currents to drive or excite elements of the magnetic field sensors. The magnetic field sensor elements receive the voltage or current and, in response to one or more of the generated magnetic fields, the magnetic field sensor elements generate sensing signals, which are transmitted to the controller 106. The controller 106 is configured to control the amount of voltage or current to the magnetic field sensors and to control the magnetic field generators 104 to generate one or more of the magnetic fields B1, B2, and B3. The controller 106 is further configured to receive the sensing signals from the magnetic field sensors and to determine the location and orientation of the sensor assembly 102 (and therefore probe 108) in relation to the magnetic fields B1, B2, and B3. The controller 106 can be implemented using firmware, integrated circuits, and/or software modules that interact with each other or are combined together. For example, the controller 106 may include computer-readable instructions/code for execution by a processor. Such instructions may be stored on a non-transitory computer-readable medium and transferred to the processor for execution. In general, the controller 106 can be implemented in any form of circuitry suitable for controlling and processing magnetic tracking signals and information.

Figure 2:
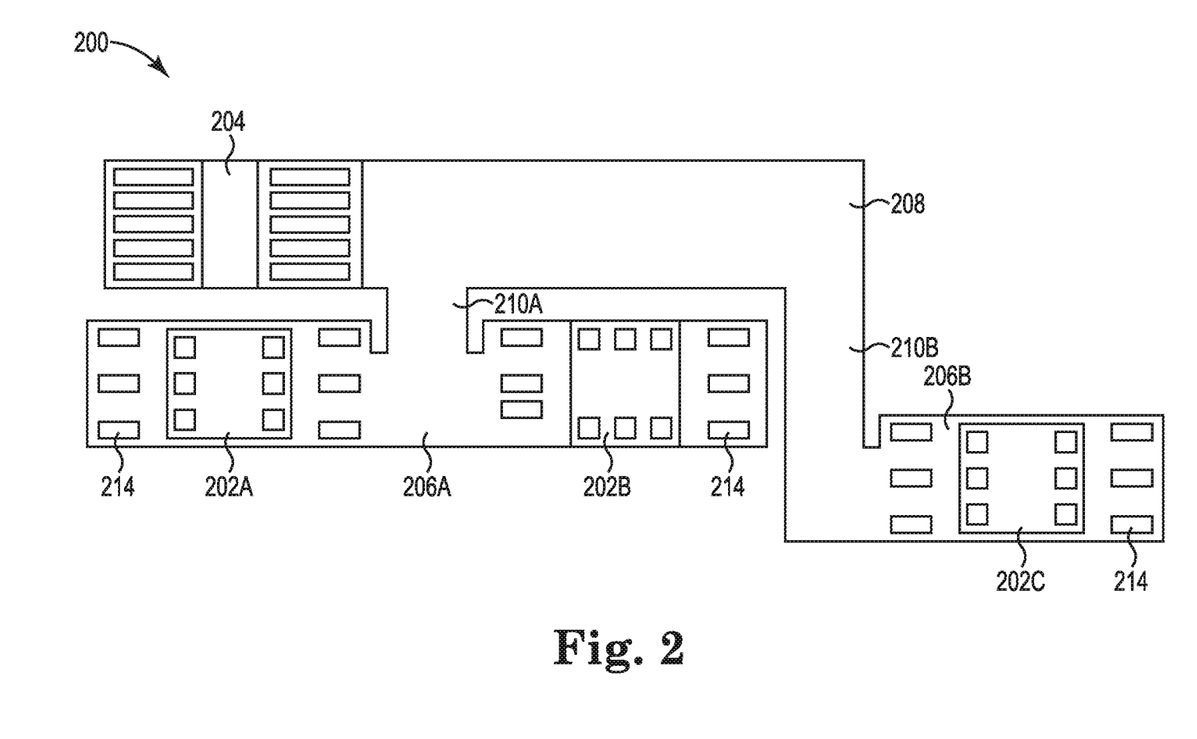
FIG. 2 shows a top-view schematic of a sensor assembly, in accordance with certain embodiments of the present disclosure.
Figure 3:
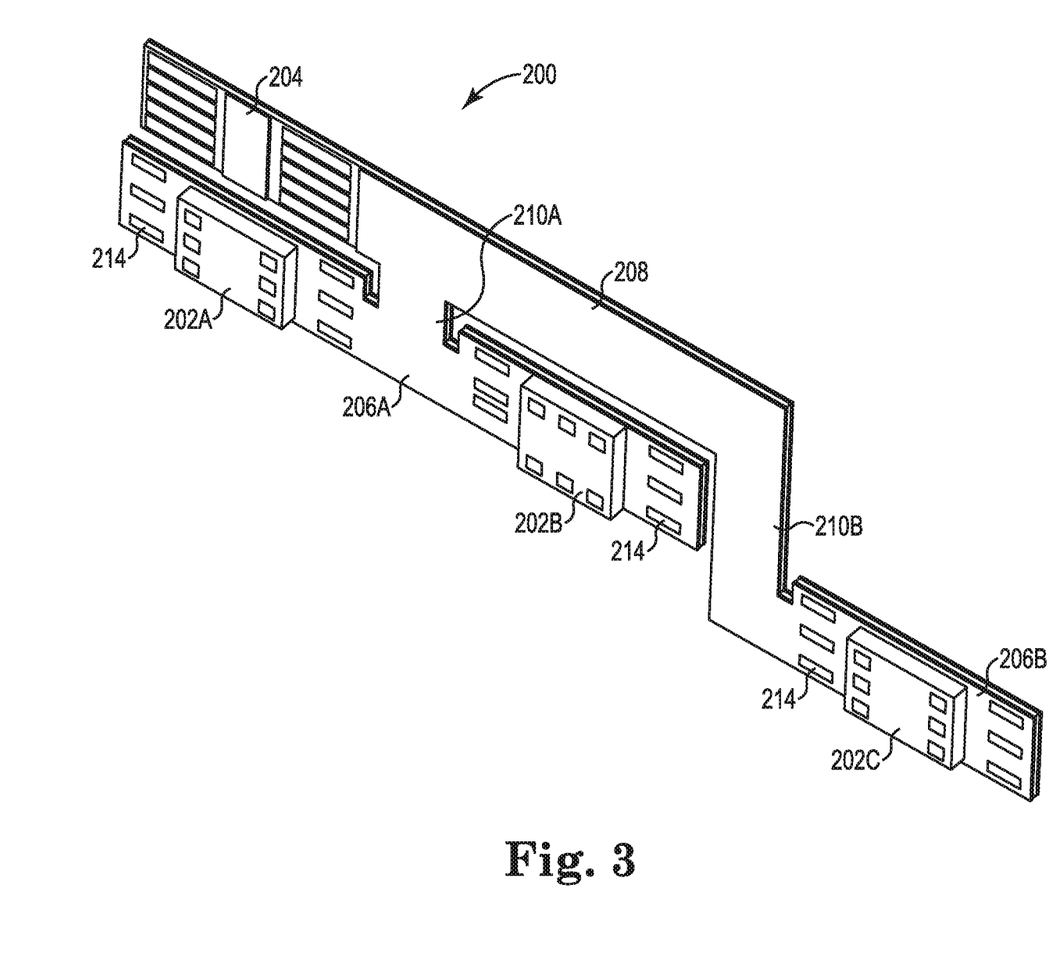
FIG. 3 shows a perspective-view schematic of the sensor assembly of FIG. 2.
Figure 4:
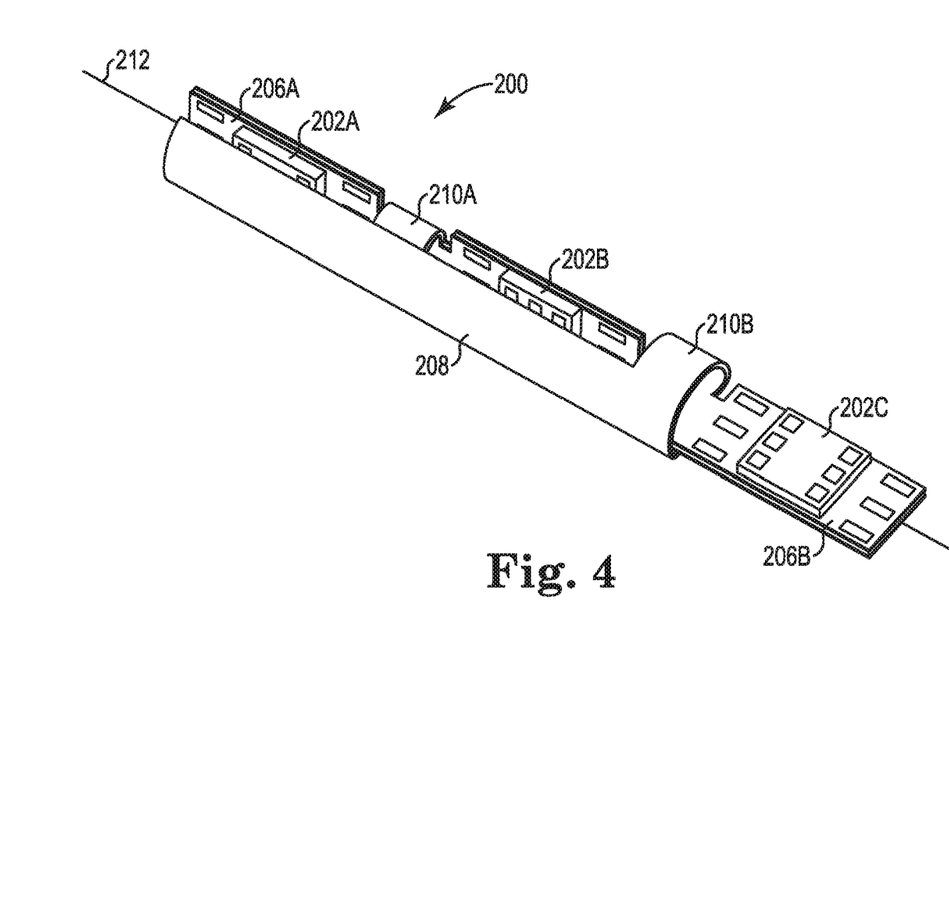
FIG. 4 shows a perspective-view schematic of the sensor assembly of FIG. 2.
Figure 5:
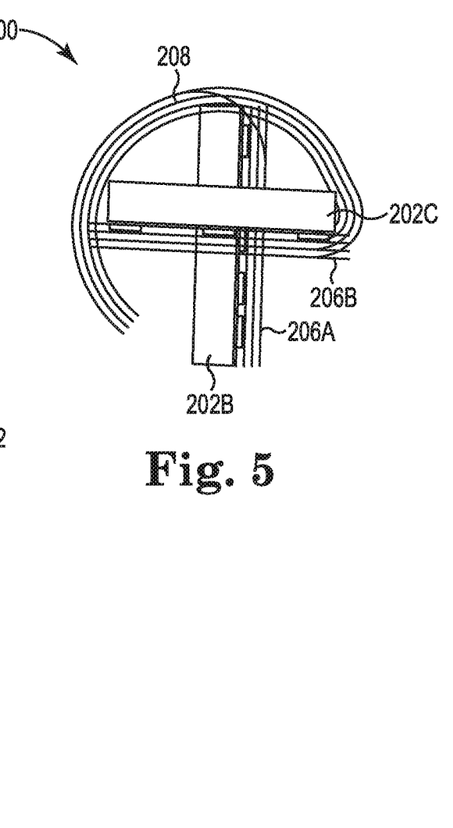
FIG. 5 shows a side-view schematic of the sensor assembly of FIG. 2.

FIG. 2 shows a top view of a sensor assembly 200 in an "unrolled" form. The sensor assembly 200 can be used in a probe (like the probe 108 in FIG. 1). FIG. 3 shows a perspective view of the sensor assembly 200 in the unrolled form. FIG. 4 shows a perspective view of the sensor assembly 200 in a "rolled" form, and FIG. 5 shows a side view of the sensor assembly 200 in the rolled form.

The sensor assembly 200 includes first, second, and third magnetic field sensors, 202A, 202B, and 202C. The magnetic field sensors 202A, 202B, and 202C can include sensors such as inductive sensing coils and/or various sensing elements such as MR sensing elements (e.g., AMR sensing elements, GMR sensing elements, TMR sensing elements, Hall effect sensing elements, CMR sensing elements, EMR sensing elements, spin Hall sensing elements, and the like), GMI sensing elements, and/or flux-gate sensing elements. The sensing elements are configured to sense magnetic fields, like those generated by the magnetic field generator 104 of FIG. 1, and generate a responsive sensing signal. In addition, the sensor assembly 200 can feature other types of sensors, such as temperature sensors, ultrasound sensors, etc. Sensing signals generated by the magnetic field sensors 202A-C can be transmitted from the sensing assembly 200 to a controller, such as the controller 106 of FIG. 1, wirelessly or via one or more conductors.

The first magnetic field sensor 202A, the second magnetic field sensor 202B, and the third magnetic field sensor 202C are shown being positioned on a common sensor assembly substrate 204, which can form part of a flex circuit. It is appreciated that the magnetic field sensors can be positioned on separate substrates that form part of a flex circuit. In some embodiments, the flex circuit is a single- or double-sided printed circuit board. In some embodiments, the flex circuit is a multi-layer flex circuit. The flex circuit can comprise LCP and/or polyimide core materials, copper clad and/or thin film metallization, and/or laminate materials or liquid dielectrics.

The substrate 204 includes a first portion 206A on which the first and second magnetic field sensors 202A and 202B are positioned and a second portion 206B on which the third magnetic field sensor 202C is positioned. The substrate 204 includes a rollable section 208, which features a first arm 210A and a second arm 210B. The rollable section 208 is positioned between the first portion 206A and the second portion 206B. As shown in FIG. 4, the rollable section 208 is configured to be rolled such that the third magnetic field sensor 202C is oriented orthogonal to the first and second magnetic field sensors 202A and 202B. The first and second arms, 210A-B, can be configured to be rolled. The first portion 206A and the second portion 206B are shown in FIG. 5 as being substantially flat. The rollable section 208 comprises a flexible material that can withstand being bent to the form shown in FIG. 4. Once rolled, the sensor assembly 200 forms a cylinder shape, which can fit into a distal portion of a probe (like the probe 108 in FIG. 1).

In some embodiments, the rollable section 208 is rolled around (i.e., extends circumferentially at least partially about) a longitudinal axis 212 of the sensor assembly 200. For example, the rollable section 208 can be rolled at least 180 degrees around the longitudinal axis 212. In other examples, the rollable section 208 can be rolled at least 360 degrees around the longitudinal axis 212 to form a full cylinder shape. In some embodiments, the rollable section 208 can be rolled between 90 and 180 degrees around the longitudinal axis 212. In some embodiments, the rollable section 208 can be rolled between 180 and 360 degrees around the longitudinal axis 212.

In the rolled form, the first magnetic field sensor 202A is oriented such that its primary sensing direction is aligned along the longitudinal axis 212 (e.g., X-axis) of the sensor assembly 200. The second magnetic field sensor 202B is oriented such that its primary sensing direction is aligned along an axis (e.g., Y-axis) orthogonal to the longitudinal axis 212. The third magnetic field sensor 202C is oriented such that its primary sensing direction is aligned along an axis (e.g., Z-axis) orthogonal to the X- and Y-axes. The first, second, and third magnetic field sensors, 202A-C, are configured to generate, in response to a magnetic field, responsive sensing signals. The sensing signals are used to determine location and orientation of the sensor assembly 200.

The magnetic field sensors, 202A-C, can be electrically coupled to the flex circuit via any connection technique known in the art. In some embodiments, the magnetic field sensors, 202A-C, are electrically coupled to conductors 214 on the substrate 204 in a flip-chip fashion, solder, fan out, through silicon vias, and the like. The conductors 214 can communicate electrical signals (e.g., sensing signals, power signals) to and from the magnetic field sensors, 202A-C, and the controller 106 of the tracking system 100.

Figure 6:
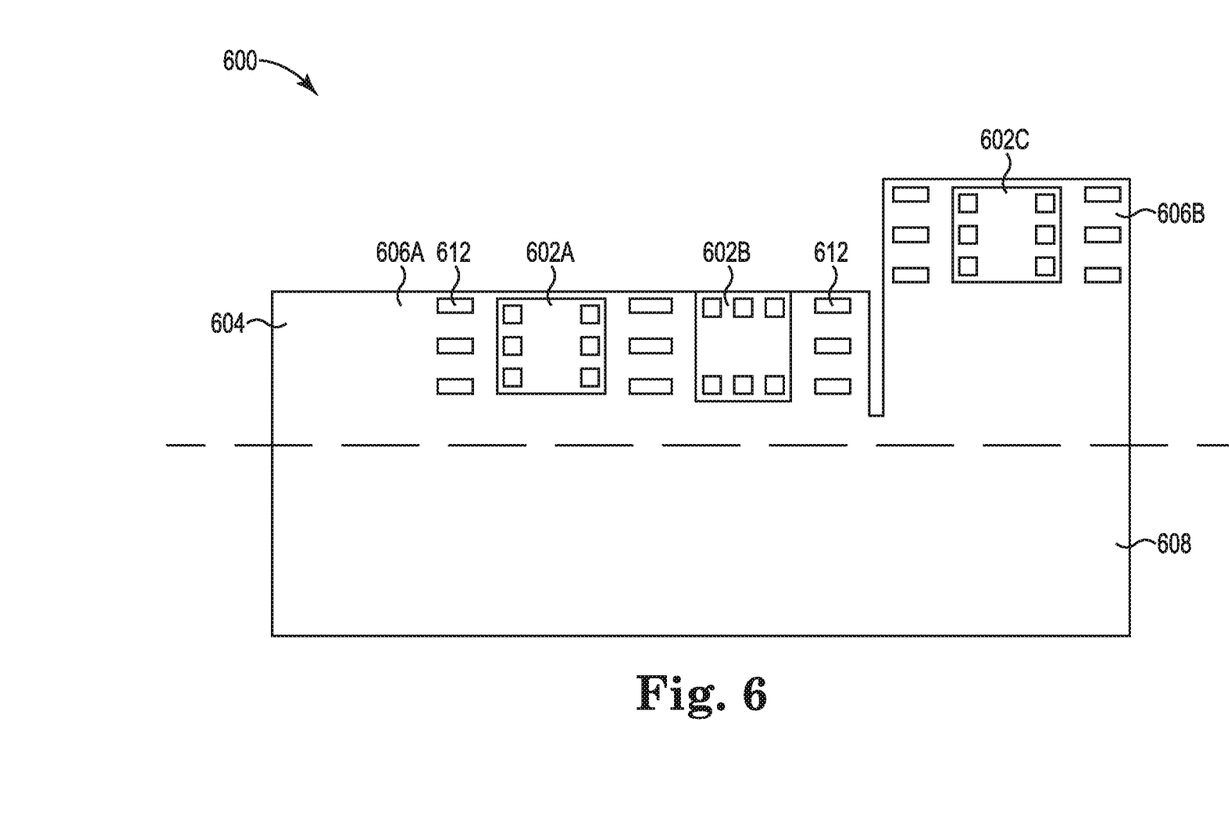
FIG. 6 shows a top-view schematic of a sensor assembly, in accordance with certain embodiments of the present disclosure.
Figure 7:
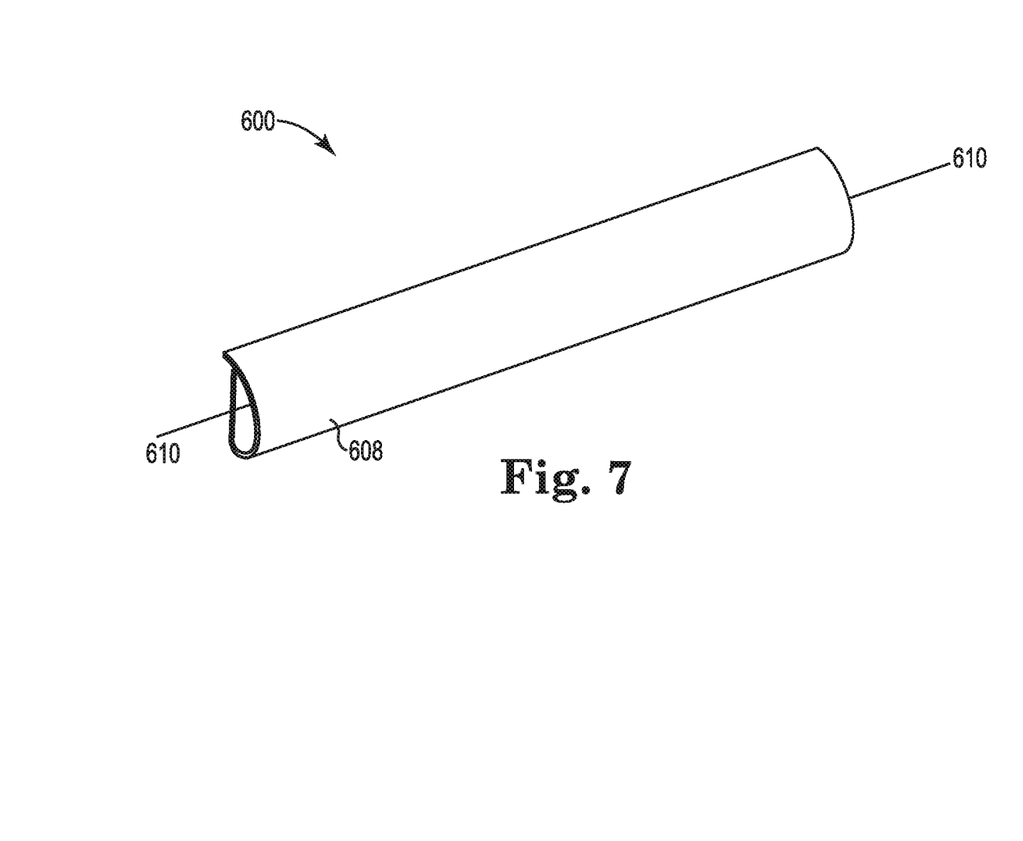
FIG. 7 shows a perspective-view schematic of the sensor assembly of FIG. 6.
Figure 8:
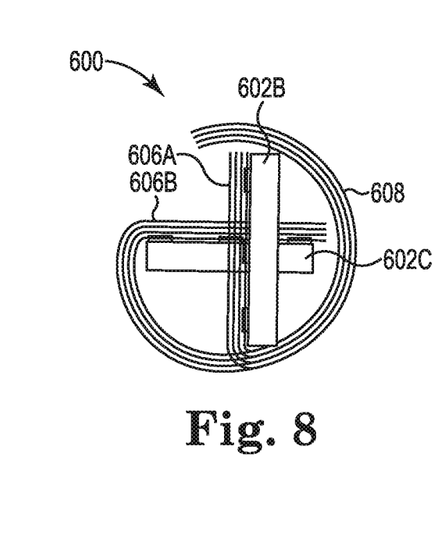
FIG. 8 shows a side-view schematic of the sensor assembly of FIG. 6.

FIG. 6 shows a top view of a sensor assembly 600 in an "unrolled" form. The sensor assembly 600 can be used in a probe (like the probe 108 in FIG. 1). FIG. 7 shows a perspective view of the sensor assembly 600 in a "rolled" form, and FIG. 8 shows a side view of the sensor assembly 600 in the rolled form.

The sensor assembly 600 includes first, second, and third magnetic field sensors, 602A, 602B, and 602C. The magnetic field sensors 602A, 602B, and 602C can include sensors such as inductive sensing coils and/or various sensing elements such as MR sensing elements (e.g., AMR sensing elements, GMR sensing elements, TMR sensing elements, Hall effect sensing elements, CMR sensing elements, EMR sensing elements, spin Hall sensing elements, and the like), GMI sensing elements, and/or flux-gate sensing elements. The MR sensing elements are configured to sense magnetic fields, like those generated by the magnetic field generator 104 of FIG. 1, and generate a responsive sensing signal. In addition, the sensor assembly 600 can feature other types of sensors, such as temperature sensors, ultrasound sensors, etc. Sensing signals generated by the magnetic field sensors 602A-C can be transmitted from the sensing assembly 600 to a controller, such as the controller 106 of FIG. 1, wirelessly or via one or more conductors.

The first magnetic field sensor 602A, the second magnetic field sensor 202B, and the third magnetic field sensor 602C are shown being positioned on a common sensor assembly substrate 604, which can form part of a flex circuit. It is appreciated that the magnetic field sensors can be positioned on separate substrates that form part of a flex circuit. In some embodiments, the flex circuit is a single- or double-sided printed circuit board. In some embodiments, the flex circuit is a multi-layer flex circuit. The flex circuit can comprise LCP and/or polyimide core materials, copper clad and/or thin film metallization, and/or laminate materials or liquid dielectrics.

The substrate 604 includes a first portion 606A on which the first and second magnetic field sensors 602A and 602B are positioned and a second portion 606B on which the third magnetic field sensor 602C is positioned. The substrate 604 includes a rollable section 608. As shown in FIGS. 7 and 8, the rollable section 608 is configured to be rolled such that the third magnetic field sensor 602C is oriented orthogonal to the first and second magnetic field sensors 602A and 602B. The rollable section 608 comprises a flexible material that can withstand being bent to the form shown in FIGS. 7 and 8. Once rolled, the sensor assembly 600 forms a cylinder shape, which can fit into a distal portion of a probe (like the probe 108 in FIG. 1). The first portion 606A and the second portion 606B are shown in FIG. 8 as being substantially flat. As shown in FIG. 6, the rollable section 608 extends the entire length of the sensor assembly 600, although it is appreciated that the rollable section can have a length shorter than the sensor assembly 600.

In some embodiments, the rollable section 608 is rolled around a longitudinal axis 610 of the sensor assembly 600. For example, the rollable section 608 can be rolled at least 180 degrees around the longitudinal axis 610. In other examples, the rollable section 608 can be rolled at least 360 degrees around the longitudinal axis 610 to form a full cylinder shape. In some embodiments, the rollable section 608 can be rolled between 90 and 180 degrees around the longitudinal axis 610. In some embodiments, the rollable section 608 can be rolled between 180 and 360 degrees around the longitudinal axis 610.

In the rolled form, the first magnetic field sensor 602A is oriented such that its primary sensing direction is aligned along the longitudinal axis 610 (e.g., X-axis) of the sensor assembly 600. The second magnetic field sensor 602B is oriented such that its primary sensing direction is aligned along an axis (e.g., Y-axis) orthogonal to the longitudinal axis 610. The third magnetic field sensor 602C is oriented such that its primary sensing direction is aligned along an axis (e.g., Z-axis) orthogonal to the X- and Y-axes. The first, second, and third magnetic field sensors, 602A-C, are configured to generate, in response to a magnetic field, responsive sensing signals. The sensing signals are used to determine location and orientation of the sensor assembly 600.

The magnetic field sensors, 602A-C, can be electrically coupled to the flex circuit via any connection technique known in the art. In some embodiments, the magnetic field sensors, 602A-C, are electrically coupled to conductors 612 on the substrate 604 in a flip-chip fashion, solder, fan out, through silicon vias, and the like. The conductors 612 can communicate electrical signals (e.g., sensing signals, power signals) to and from the magnetic field sensors, 602A-C, and the controller 106 of the tracking system 100.

Figure 9:
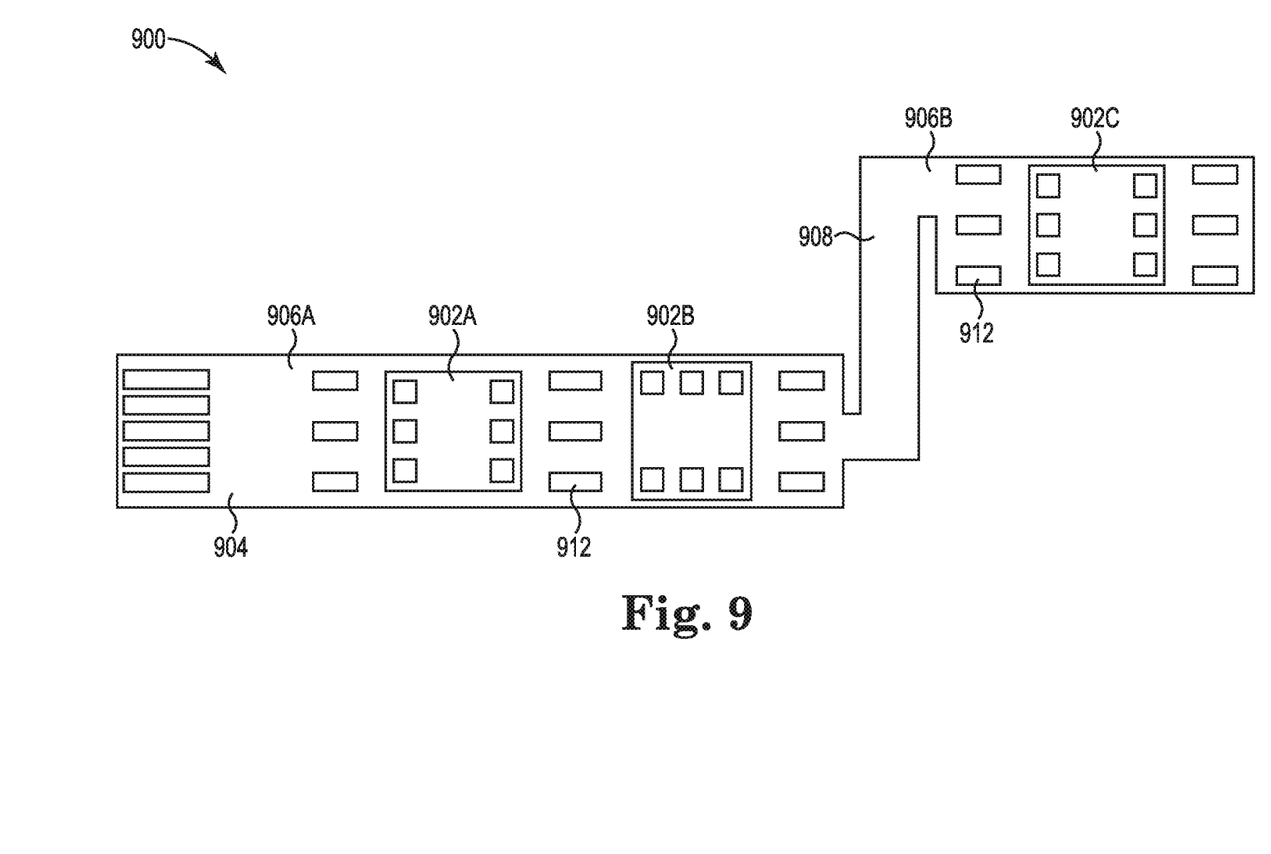
FIG. 9 shows a top-view schematic of a sensor assembly, in accordance with certain embodiments of the present disclosure.
Figure 10:
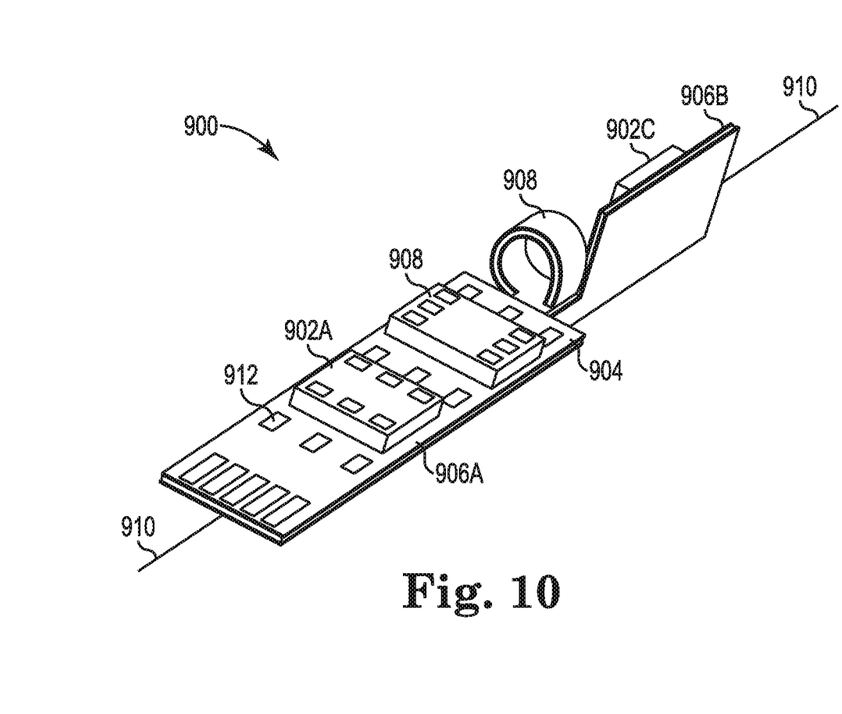
FIG. 10 shows a perspective-view schematic of the sensor assembly of FIG. 9.
Figure 11:
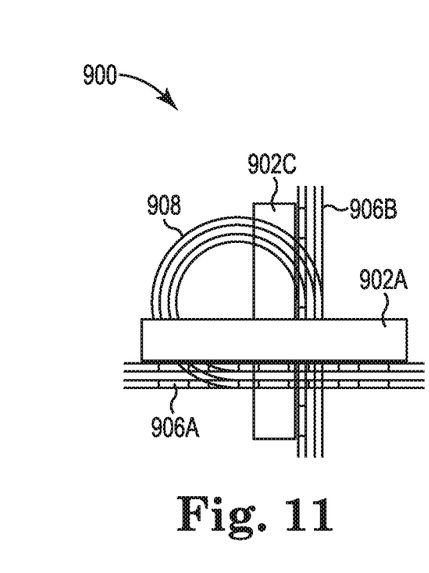
FIG. 11 shows a side-view schematic of the sensor assembly of FIG. 9.

FIG. 9 shows a top view of a sensor assembly 900 in an "unrolled" form. The sensor assembly 900 can be used in a probe (like the probe 108 in FIG. 1). FIG. 10 shows a perspective view of the sensor assembly 900 in a "rolled" form, and FIG. 11 shows a side view of the sensor assembly 900 in the rolled form.

The sensor assembly 900 includes first, second, and third magnetic field sensors, 902A, 902B, and 902C. The magnetic field sensors 902A, 902B, and 902C can include sensors such as inductive sensing coils and/or various sensing elements such as MR sensing elements (e.g., AMR sensing elements, GMR sensing elements, TMR sensing elements, Hall effect sensing elements, CMR sensing elements, EMR sensing elements, spin Hall sensing elements, and the like), GMI sensing elements, and/or flux-gate sensing elements. The MR sensing elements are configured to sense magnetic fields, like those generated by the magnetic field generator 104 of FIG. 1, and generate a responsive sensing signal. In addition, the sensor assembly 900 can feature other types of sensors, such as temperature sensors, ultrasound sensors, etc. Sensing signals generated by the magnetic field sensors 902A-C can be transmitted from the sensing assembly 900 to a controller, such as the controller 106 of FIG. 1, wirelessly or via one or more conductors.

The first magnetic field sensor 902A, the second magnetic field sensor 902B, and the third magnetic field sensor 902C are shown being positioned on a common sensor assembly substrate 904, which can form part of a flex circuit. It is appreciated that the magnetic field sensors can be positioned on separate substrates that form part of a flex circuit. In some embodiments, the flex circuit is a single- or double-sided printed circuit board. In some embodiments, the flex circuit is a multi-layer flex circuit. The flex circuit can comprise LCP and/or polyimide core materials, copper clad and/or thin film metallization, and/or laminate materials or liquid dielectrics.

The substrate 904 includes a first portion 906A on which the first and second magnetic field sensors 902A and 902B are positioned and a second portion 906B on which the third magnetic field sensor 902C is positioned. The substrate 904 includes a rollable section 908 that is positioned and extends between the first portion 906A and the second portion 906B. As shown in FIGS. 10 and 11, the rollable section 908 is configured to be rolled such that the third magnetic field sensor 902C is oriented orthogonal to the first and second magnetic field sensors 902A and 902B. The rollable section 908 comprises a flexible material that can withstand being bent to the form shown in FIGS. 10 and 11. Once rolled, the sensor assembly 900 can fit into a distal portion of a probe (like the probe 108 in FIG. 1). The first portion 906A and the second portion 906B are shown in FIG. 11 as being substantially flat.

In some embodiments, the rollable section 908 is rolled around a longitudinal axis 910 of the sensor assembly 900. For example, the rollable section 908 can be rolled at least 180 degrees around the longitudinal axis 910. In other examples, the rollable section 908 can be rolled at least 360 degrees around the longitudinal axis 610 to form a full cylinder shape. In some embodiments, the rollable section 908 can be rolled between 90 and 180 degrees around the longitudinal axis 910. In some embodiments, the rollable section 908 can be rolled between 180 and 360 degrees around the longitudinal axis 910. The rollable section 908 in FIGS. 9-11 has a relatively shorter length along the longitudinal axis 910 compared to the overall length of the sensor assembly 900. When unrolled, the rollable section 908 is shown as forming an "S" shape, although other shapes are contemplated.

In the rolled form, the first magnetic field sensor 902A is oriented such that its primary sensing direction is aligned along the longitudinal axis 910 (e.g., X-axis) of the sensor assembly 900. The second magnetic field sensor 902B is oriented such that its primary sensing direction is aligned along an axis (e.g., Y-axis) orthogonal to the longitudinal axis 910. The third magnetic field sensor 902C is oriented such that its primary sensing direction is aligned along an axis (e.g., Z-axis) orthogonal to the X- and Y-axes. The first, second, and third magnetic field sensors, 902A-C, are configured to generate, in response to a magnetic field, responsive sensing signals. The sensing signals are used to determine location and orientation of the sensor assembly 900.

The magnetic field sensors, 902A-C, can be electrically coupled to the flex circuit via any connection technique known in the art. In some embodiments, the magnetic field sensors, 902A-C, are electrically coupled to conductors 912 on the substrate 904 in a flip-chip fashion, solder, fan out, through silicon vias, and the like. The conductors 912 can communicate electrical signals (e.g., sensing signals, power signals) to and from the magnetic field sensors, 902A-C, and the controller 106 of the tracking system 100.

It should be noted that, for simplicity and ease of understanding, the elements described above and shown in the figures are not drawn to scale and may omit certain features. As such, the drawings do not necessarily indicate the relative sizes of the elements or the non-existence of other features.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A sensor assembly comprising:
    a substrate including a first portion, a second portion, and a rolled section positioned between the first portion and the second portion, wherein the rolled section extends circumferentially about a longitudinal axis of the sensor assembly, wherein the first portion is not rolled, wherein the second portion is not rolled;
    a first magnetic field sensor coupled to the first portion, wherein the first magnetic field sensor has a first primary sensing direction aligned with the longitudinal axis of the sensor assembly; and
    a second magnetic field sensor coupled to the second portion, wherein the rolled section is shaped such that the second magnetic field sensor is oriented with respect to the first magnetic field sensor so that the second magnetic field sensor has a second primary sensing direction aligned with a first orthogonal axis that is orthogonal to the longitudinal axis.

2. The sensor assembly of claim 1, further comprising a third magnetic field sensor coupled to the first portion and oriented with respect to the first magnetic field sensor such that the third magnetic field sensor has a third primary sensing direction aligned with a second orthogonal axis that is orthogonal to the longitudinal axis.

3. The sensor assembly of claim 2, wherein the first, the second, and the third magnetic field sensors include one of magneto-resistive sensing elements, giant magneto-impedance sensing elements, and flux-gate sensing elements.

4. The sensor assembly of claim 3, wherein the substrate forms part of a flex circuit.

5. The sensor assembly of claim 3, wherein the first, the second, and the third magnetic field sensors are coupled to conductors by a flip-chip approach, solder connections, fan-out, or through silicon vias.

6. The sensor assembly of claim 2, wherein the rolled section extends circumferentially only between 90 and 180 degrees about the longitudinal axis.

7. The sensor assembly of claim 2, wherein the rolled section extends circumferentially only between 180 and 360 degrees about the longitudinal axis.

8. The sensor assembly of claim 1, wherein the rolled section forms a cylinder shape.

9. The sensor assembly of 8, wherein the first portion and the second portion are substantially flat and do not form a cylinder shape.

10. The sensor assembly claim 9, wherein the rolled section has a length along the longitudinal axis, wherein the length is substantially equal to an overall length of the sensor assembly.

11. The sensor assembly of claim 10, wherein the rolled section includes a first arm and a second arm.

12. The sensor assembly of claim 9, wherein the first portion and the second portion are arranged orthogonally with respect to each other.

13. The sensor assembly of claim 1, wherein the first magnetic field sensor and the second magnetic field sensor are not positioned on a rolled portion of the substrate.

14. A medical probe comprising:
    a distal portion having a sensor assembly disposed therein, wherein the sensor assembly comprises:
        a substrate including a first portion, a second portion, and a rolled section positioned between the first portion and the second portion, wherein the rolled section extends circumferentially about a longitudinal axis of the sensor assembly, wherein the first portion is unrolled, wherein the second portion is unrolled;
        a first magnetic field sensor coupled to the first portion, wherein the first magnetic field sensor has a first primary sensing direction aligned with the longitudinal axis of the sensor assembly; and
        a second magnetic field sensor coupled to the second portion, wherein the rolled section is shaped such that the second magnetic field sensor is oriented with respect to the first magnetic field sensor so that the second magnetic field sensor has a second primary sensing direction aligned with a first orthogonal axis that is orthogonal to the longitudinal axis.

15. The medical probe of claim 14, further comprising a third magnetic field sensor coupled to the first portion and oriented with respect to the first magnetic field sensor such that the third magnetic field sensor has a third primary sensing direction aligned with a second orthogonal axis that is orthogonal to the longitudinal axis.

16. The medical probe of claim 15, wherein the first, the second, and the third magnetic field sensors include one of magneto-resistive sensing elements, giant magneto-impedance sensing elements, and flux-gate sensing elements.

17. The medical probe of claim 15, wherein the rolled section forms a cylinder shape, and wherein the first portion and the second portion are substantially flat and do not form a cylinder shape.

18. A medical system comprising:
    a medical probe including a distal portion having a sensor assembly disposed therein, wherein the sensor assembly comprises:
        a substrate including a first portion, a second portion, and a rolled section positioned between the first portion and the second portion, wherein the rolled section is rolled and extends circumferentially about a longitudinal axis of the sensor assembly, wherein the first portion is unrolled, wherein the second portion is unrolled;
        a first magnetic field sensor coupled to the first portion, wherein the first magnetic field sensor has a first primary sensing direction aligned with the longitudinal axis of the sensor assembly; and
        a second magnetic field sensor coupled to the second portion, wherein the rolled section is shaped such that the second magnetic field sensor is oriented with respect to the first magnetic field sensor so that the second magnetic field sensor has a second primary sensing direction aligned with an first orthogonal axis that is orthogonal to the longitudinal axis;

a magnetic field generator configured to generate a multi-dimensional magnetic field in a volume including the medical probe and a patient; and a processor operable to receive outputs from the sensor assembly to determine a position of the sensor assembly within the volume.

19. The medical system of claim 18, wherein the sensor assembly further comprises a third magnetic field sensor coupled to the first portion and oriented with respect to the first magnetic field sensor such that the third magnetic field sensor has a third primary sensing direction aligned with a second orthogonal axis that is orthogonal to the longitudinal axis.

20. The medical system of claim 19, wherein the first, the second, and the third magnetic field sensors include one of magneto-resistive sensing elements, giant magneto-impedance sensing elements, and flux-gate sensing elements.

* * * * *